United States Patent
Schroeder et al.

(10) Patent No.: US 11,045,405 B2
(45) Date of Patent: Jun. 29, 2021

(54) SHINE CONDITIONERS

(71) Applicant: Henkel AG & Co. KGaA, Duesseldorf (DE)

(72) Inventors: Thomas Schroeder, Hamburg (DE); Soeren Scheele, Pinneberg (DE); Manuela Mette, Kleinfeld (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 16/281,946

(22) Filed: Feb. 21, 2019

(65) Prior Publication Data
US 2019/0262247 A1    Aug. 29, 2019

(30) Foreign Application Priority Data

Feb. 23, 2018 (DE) .................... 10 2018 202 803.6

(51) Int. Cl.
| | | |
|---|---|---|
| *A61K 8/44* | (2006.01) | |
| *A61Q 5/12* | (2006.01) | |
| *A61Q 5/02* | (2006.01) | |
| *A61K 8/42* | (2006.01) | |
| *A61K 8/46* | (2006.01) | |
| *A61K 8/362* | (2006.01) | |
| *A61K 8/365* | (2006.01) | |

(52) U.S. Cl.
CPC ................ *A61K 8/44* (2013.01); *A61K 8/362* (2013.01); *A61K 8/365* (2013.01); *A61K 8/42* (2013.01); *A61K 8/463* (2013.01); *A61Q 5/02* (2013.01); *A61Q 5/12* (2013.01); *A61K 2800/30* (2013.01); *A61K 2800/34* (2013.01)

(58) Field of Classification Search
CPC .................................................. A61Q 5/00–12
See application file for complete search history.

(56) References Cited

U.S. PATENT DOCUMENTS 6,274,128 B1    8/2001   Bergmann et al.

FOREIGN PATENT DOCUMENTS

| | | | |
|---|---|---|---|
| CN | 108295006 A | 7/2018 | |
| DE | 102012205083 A1 | 10/2013 | |
| DE | 102015223028 A1 * | 6/2016 | ............. A61K 8/416 |
| DE | 102015223028 A1 | 6/2016 | |
| EP | 2165697 A1 | 3/2010 | |

OTHER PUBLICATIONS

DE 102015223028A1—machine translation of Description and Claims.*

* cited by examiner

*Primary Examiner* — H. Sarah Park
(74) *Attorney, Agent, or Firm* — Lorenz & Kopf, LLP

(57) ABSTRACT

The present disclosure relates to hair treatment agents and methods for improving nourishment properties of hair. An exemplary hair treatment agent includes, in a cosmetic carrier, trimethylglycine, an amidoamine of a specific formula and an esterquat of a specific formula. An exemplary hair treatment agent is suitable for improving the nourishment properties of hair, in particular for improving the combability and ease of detangling of wet and dry hair, and also the feel, shine and static properties of hair.

2 Claims, No Drawings

SHINE CONDITIONERS

CROSS-REFERENCE TO RELATED APPLICATION

This application claims priority to German Patent Application No. 10 2018 202 803.6, filed Feb. 23, 2018, which is incorporated herein by reference in its entirety.

TECHNICAL FIELD

The present disclosure relates to nourishing hair treatment agents based on trimethylglycine and specific amidoamines and esterquats. The present disclosure also relates to the use of the hair treatment agents to improve the nourishment properties of hair, in particular to improve hair shine.

BACKGROUND

The importance of haircare products that have as long-lasting an effect as possible is increased not least by the severe stressing of hair caused for example by dyeing or permanent waving, frequent cleaning with shampoos and subsequent drying with a hairdryer, and environmental stresses.

The known active substances, however, cannot cover all requirements adequately.

Due to the rising number of intolerances there is an increasing consumer need for simple cosmetic hair treatment agents with a high content of active substances and auxiliaries of natural origin with very good hair-nourishing properties and good biodegradability.

The compounds that have long been known as effective active haircare substances include cationic surfactants, such as quaternary ammonium compounds of the mono-, di- and/or trialkylammonium compound and esterquat type.

These active substances, however, are being overshadowed due to their inadequate biodegradability, and esterquats have the disadvantage that they often leave the hair looking lackluster, which is not desired. In the past, they were in many cases combined with silicones in order to overcome this disadvantage and achieve an improved nourishing effect Silicones, however, are also criticized from an ecological viewpoint, and therefore their use is preferably omitted in haircare agents.

In document DE 102015223028 a combination of esterquats and specific further cationic compounds was proposed. Haircare agents could thus be provided that provide the hair with improved detangling and combability properties, an improved feel, and more volume and shine.

With regard to the combability and ease of detangling of dry hair, however, there is still a need for optimization. In addition, cationic nourishing substances sometimes lead to flyaway hair, which is undesirable and problematic in particular for use on dry hair and/or very fine hair.

BRIEF SUMMARY

Hair treatment agents and methods for improving the nourishment properties of hair are provided. An exemplary hair treatment agent includes, in a cosmetic carrier, (a) trimethylglycine, (b) at least one amidoamine of formula (I)

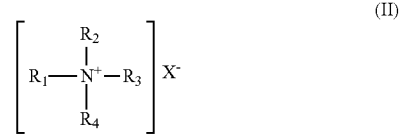

in which $R_1$ stands for a saturated or unsaturated, branched or unbranched alk(en)yl group with from 19 to 30 carbon atoms, $R_2$, $R_3$ independently of one another stand for —H or for a $C_1$-$C_4$ alkyl group, and x stands for an integer from 2 to 6, and (c) at least one esterquat of formula (II),

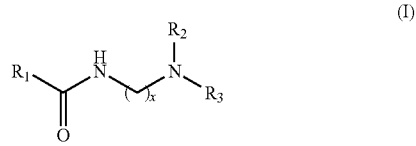

in which $X^-$ stands for a halide, methyl sulfate, ethyl sulfate, maleate, fumarate, oxalate, tartrate, citrate, lactate or acetate ion, $R_1$, $R_2$ are the same or different and stand for an $C_1$-$C_4$ alkyl group, and $R_3$, $R_4$ are the same or different and stand for a —$CH_2$—$CH(R_5)$—$OR_6$ grouping, in which $R_5$ stands for a $C_1$-$C_6$ alkyl group, and $R_6$ stands for an acyl group of an at least monounsaturated carboxylic acid with a C-chain length of from 18 to 24 carbon atoms or for the acyl group of isostearic acid.

An exemplary method for improving the nourishment properties of hair includes applying a hair treatment agent to the hair. The hair treatment agent includes, in a cosmetic carrier, (a) trimethylglycine, (b) at least one amidoamine of formula (I),

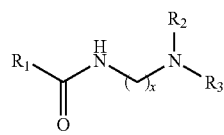

in which $R_1$ stands for a saturated or unsaturated, branched or unbranched alk(en)yl group with from 19 to 30 carbon atoms, $R_2$, $R_3$ independently of one another stand for —H or for a $C_1$-$C_4$ alkyl group, and x stands for an integer from 2 to 6, and (c) at least one esterquat of formula (II),

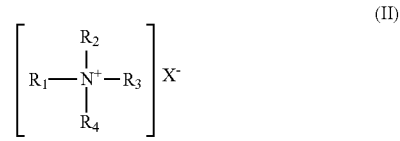

in which $X^-$ stands for a halide, methyl sulfate, ethyl sulfate, maleate, fumarate, oxalate, tartrate, citrate, lactate or acetate ion, $R_1$, $R_2$ are the same or different and stand for an $C_1$-$C_4$ alkyl group, and $R_3$, $R_4$ are the same or different and stand for a —$CH_2$—$CH(R_5)$—$OR_6$ grouping, in which $R_5$ stands for a $C_1$-$C_6$ alkyl group, and $R_6$ stands for an acyl group of an at least monounsaturated carboxylic acid with a C-chain length of from 18 to 24 carbon atoms or for the acyl group of isostearic acid.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

The object of the present application was therefore to provide a hair treatment agent that has high nourishing performance and ensures an optimal balance between long-lasting and sustainable nourishment, and good compatibility and biodegradability.

Here, the supporting effect of silicones and/or mineral oils ideally shall be spared.

A further object of the present application was that of developing hair treatment agents with which the hair shine can be improved.

It has been found that, by means of the combination of trimethylglycine with specific amidoamines and esterquats, hair treatment agents with excellent nourishing effect can be provided. The agents are very highly compatible with the skin and have good environmental compatibility.

In particular, combability and ease of detangling of wet and dry hair and also the feel, shine and static properties of hair could be improved by application of the agents, without the need to use additional nourishing substances, such as silicones or mineral oils.

The hair treatment agents additionally can be produced easily and without difficulty and are also stable under storage, even with fluctuations in temperature.

A first subject of this application is thus a hair treatment agent which contains, in a cosmetic carrier
a) trimethylglycine
b) at least one amidoamine of formula (I)

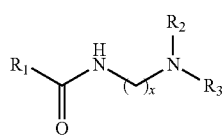

(I)

in which
$R_1$ stands for a saturated or unsaturated, branched or unbranched alk(en)yl group with from about 19 to about 30 carbon atoms,
$R_2$, $R_3$ independently of one another stand for —H or for a $C_1$-$C_4$ alkyl group, and
x stands for an integer from about 2 to about 6, and
c) at least one esterquat of formula (II),

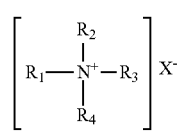

(II)

in which
$R_1$, $R_2$ are the same or different and stand for an $C_1$-$C_4$ alkyl group, alkyl
$R_3$, $R_4$ are the same or different and stand for a —$CH_2$—$CH(R_5)$—$OR_6$ grouping, in which
$R_5$ stands for a $C_1$-$C_6$ alkyl group,
$R_6$ stands for an acyl group of an at least monounsaturated carboxylic acid with a C-chain length of from about 18 to about 24 carbon atoms or for the acyl group of isostearic acid, and
$X^-$ stands for a halide, methyl sulfate, ethyl sulfate, maleate, fumarate, oxalate, tartrate, citrate, lactate or acetate ion.

Suitable hair treatment agents in the sense of the present disclosure are, for example, hair shampoos, hair conditioners, conditioning shampoos, hairsprays, hair rinses, hair masks, hair packs, hair tonics, perm fixing solutions, coloring shampoos, hair dyes, hair setting products, hair smoothing products, hairstyling preparations, blow-dry lotions, styling mousses, hair gels, hair wax, or combinations thereof.

Hair treatment agents as contemplated herein are particularly preferably understood to be leave-on or rinse-off hair-conditioning agents, which can be formulated in any commercially conventional form.

Particularly preferred hair treatment agents as contemplated herein, in accordance with a first preferred embodiment, contain (in relation to the weight of the total agent)
from about 0.05 to about 10.00% by weight trimethylglycine a),
from about 0.01 to about 2.00% by weight of at least one amidoamine b) according to formula (I),
from about 0.01 to about 10.00% by weight of at least one esterquat c) according to formula (II), The hair treatment agents as contemplated herein contain the active substances a) to c) in a cosmetic carrier. This is preferably understood within the scope of the present disclosure to mean an aqueous or aqueous-alcoholic carrier.

The cosmetic carrier preferably contains at least about 75% by weight, more preferably at least about 77% by weight, particularly preferably at least about 78% by weight, and in particular preferably about 80% by weight of water.

Furthermore, the cosmetic carrier may contain from about 0.50 to about 15% by weight, preferably from about 0.75 to about 12.50% by weight, and in particular from about 1.00 to about 10.00% by weight of at least one alcohol.

Suitable alcohols are, for example, ethanol, ethyldiglycol, 1-propanol, 2-propanol, isopropanol, 1,2-propylene glycol, glycerol, diglycerol, triglycerol, 1-butanol, 2-butanol, 1,2-butanediol, 1,3-butanediol, 1-pentanol, 2-pentanol, 1,2-pentanediol, 1,5-pentanediol, 1, hexanol, 2-hexanol, 1,2-hexanediol, 1,6-hexanediol, polyethylene glycols, sorbitol, sorbitan, benzyl alcohol, phenoxyethanol or mixtures of these alcohols.

Polyols are particularly preferred because it has been found that polyols further support the nourishing effect of active substances a) to c) in the hair treatment agents as contemplated herein. In addition, a certain polyol content can contribute to improved solubilization of any oils contained in the hair treatment agents, whereby for example it is possible to dispense with additional polymeric stabilizers.

A polyol that is preferred in particular is glycerol, which can be used in the agents as contemplated herein in the aforementioned amounts.

In a preferred embodiment, agents as contemplated herein therefore additionally contain from about 0.50 to about 10.00% by weight of at least one polyol, preferably from about 1.00 to about 10.00% by weight of glycerol.

A first essential component of the active nourishing substance mixture as contemplated herein in the hair treatment agents as contemplated herein is trimethylglycine (betaine). Trimethylglycine is an amino acid derivative that is well known for use in cosmetic agents and that is obtainable from natural sources, such as sugarcane molasses. It is offered commercially for example by the company Evonik under the name Tego® Natural Betaine and is used as a humectant in preparations for treatment of the skin and as a solidifying active substance in hair treatment agents.

It was found that the hair-nourishing properties of the specific amidoamines b) and esterquats c) can be improved further by adding trimethylglycine. In particular, the ease of detangling and combability properties of dry hair and the soft feel of the hair as far as the tips can be improved by the combination of the three active substances. In addition, the problem of statically charged hair can thus be significantly reduced.

Trimethylglycine is used in the hair treatment agents as contemplated herein (in relation to the weight of the total agent) preferably in an amount from about 0.05 to about 10.00% by weight, more preferably from about 0.10 to about 8.00% by weight, particularly preferably from about 0.50 to about 6.00% by weight, very particularly preferably from about 0.75 to about 5.00% by weight, and in particular from about 1.00 to about 4.00% by weight.

A second essential component of the nourishing active substance mixture in the hair treatment agents as contemplated herein is an amidoamine b) of formula (I),

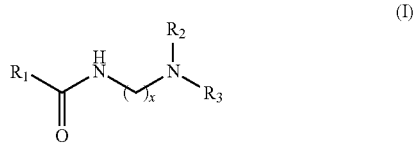

in which
$R_1$ stands for a saturated or unsaturated, branched or unbranched alk(en)yl group with from about 19 to about 30 carbon atoms,
$R_2$, $R_3$ independently of one another stand for hydrogen or for a $C_1$-$C_4$ alkyl group, and
x stands for an integer from about 2 to about 6.

Amidoamines b) of formula (I) give hair a noticeable, soft, smooth feel, without weighing it down. It has been found that, in particular, amidoamines b) with an alk(en)yl group ($R_1$) comprising more than about 19 C atoms additionally improve the combability and are better suited than the amidoamines usually used in the prior art (alk(en)yl group with ≤18 C atoms) for preventing an overcondiitoning effect.

Amidoamines b) that are particularly suitable are therefore those according to formula (I), in which
$R_1$ stands for an alkenyl group having from about 20 to about 24 carbon atoms.
$R_2$ and $R_3$ stand for methyl groups, and
x stands for the numbers 2, 3 or 4.

Amidoamines b) according to formula (I) which are selected from the amidoamines b) known under the INCI name Brassicamidopropyl Dimethylamine are in particular preferred for the use in the hair treatment agents as contemplated herein.

Such amidoamines b) are commercially available from various providers and are particularly suited for use in the agents contemplated herein; for example Kerabase® LC from the company Inolex Personal Care Ingredients, Pro-Condition® 22 from the company Inolex Personal Care Ingredients and/or Amidet® APA-22 from the company Kao Corporation.

The one or more amidoamine(s) b) is (are) used in the hair treatment agents as contemplated herein (in relation to the weight of the total agent) preferably in an amount from about 0.01 to about 2.00% by weight, more preferably from about 0.05 to about 1.75% by weight, particularly preferably from about 0.10 to about 1.50% by weight, very particularly preferably from about 0.20 to about 1.25% by weight, and in particular from about 0.25 to about 1.00% by weight.

A third essential component of the nourishing active substance mixture in the hair treatment agents as contemplated herein is an esterquat c) of formula (II),

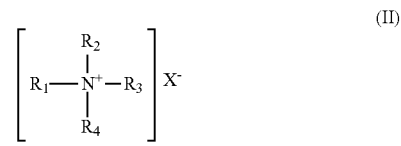

in which
$R_1$, $R_2$ are the same or different and stand for an $C_1$-$C_4$ alkyl group,
$R_3$, $R_4$ are the same or different and stand for a —$CH_2$—$CH(R_5)$—$OR_6$ grouping, in which
$R_5$ stands for a $C_1$-$C_6$ alkyl group,
$R_6$ stands for an acyl group of an at least monounsaturated carboxylic acid with a C-chain length of from about 18 to about 24 carbon atoms or for the acyl group of isostearic acid, and
$X^-$ stands for a halide, methyl sulfate, ethyl sulfate, maleate, fumarate, oxalate, tartrate, citrate, lactate or acetate ion.

Esterquats c) intensify the hair-conditioning effect of the amidoamines b) and improve in particular the feel of the hair within the active substance combination a)-c). Due to the balanced ratio by weight of the esterquats c) and the amidoamines b), the hair shine could be improved in addition.

It has been found that particularly good hair-conditioning results can be attained with esterquats c) which contain unsaturated and/or branched acyl groups $R_6$ of a specific C-chain length.

Particularly preferred esterquats c) are therefore selected from compounds of formula (II), in which
$R_1$, $R_2$ are the same and stand for a methyl group,
$R_3$, $R_4$ are the same and stand for a —$CH_2$—$CH(R_5)$—$OR_6$ grouping, in which
$R_5$ stands for a methyl group,
$R_6$ stands for the acyl group of oleic acid or for the acyl group of isostearic acid.
$X^-$ stands for a chloride or a methylsulfate ion.

Very particularly preferred are esterquats c) which contain a mixture of compounds of formula (II) (II.1 and II.2), in which
$R_6$ stands for the acyl group of oleic acid (II.1) and
$R_6$ stands for the acyl group of isostearic acid (II.2).

Particularly preferred are esterquats c) according to formula (II) which are known under the name bis(isostearoyl/oleoyl isopropyl) dimonium methosulfate (INCI name: Quaternium-98) and are commercially available for example under the name Varisoft® EQ 100 from the company Evonik The one or more esterquat(s) b) is (are) used in the hair treatment agents as contemplated herein (in relation to the weight of the total agent) preferably in an amount from about 0.01 to about 10.00% by weight, more preferably from about 0.05 to about 8.00% by weight, particularly preferably from about 0.10 to about 6.00% by weight, very particularly preferably from about 0.20 to about 4.00% by weight, and in particular from about 0.25 to about 2.00% by weight.

The best haircare results could be attained if the at least one amidoamine b) and the at least one esterquat c) were used in the active substance mixture a)-c) in a specific weight ratio.

It has proven to be particularly preferred if the ratio by weight of amidoamine b) to esterquat c) lies in the range of from about 1:5 to about 1:1 and in particular from about 1:4 to about 1:2.

In a consumer test it was found that all objectives in respect pf nourishment and stability of the compositions can be achieved with the active substance combination a)-c) in the hair treatment agents as contemplated herein. The additional incorporation of further cationic active nourishing substances, such as further cationic surfactants and/or cationic polymers, is not necessary.

In a further preferred embodiment the hair treatment agents as contemplated herein, besides the amidoamines b) and the esterquats c), therefore do not contain any further cationic (or cationizable) nourishing substances, in particular no further cationic (or cationizable) surfactants and/or cationic polymers.

In order to further increase the nourishment and/or rheological properties of the agents as contemplated herein it can be advantageous of they also contain at least one cosmetic oil.

Suitable cosmetic oils in the sense of the present disclosure are understood to mean oil bodies that have a melting point below about 50° C., particularly preferably below about 47° C., very particularly preferably below about 44° C., most preferably below 4 about 0° C. Most preferred are cosmetic oils which are flowable at a temperature below about 40° C.

Preferred cosmetic oils are natural vegetable oils.

Vegetable oils (and/or butters)—even when used at low concentrations—can further increase the aforementioned conditioning advantages on the hair in combination with the active substance combination a), b), c), without a buildup effect occurring with regular use. In addition, vegetable oils (and/or butters) in the nourishing active substance mixture of the hair treatment agents as contemplated herein also contribute to the improvement in hair shine.

Examples of natural vegetable oil suitable as contemplated herein are, for example, amaranth seed oil, apricot kernel oil, argan oil, avocado oil, babassu oil, cottonseed oil, borage seed oil, camelina oil, canola oil, cranberry oil, safflower oil, peanut oil, pomegranate seed oil, grapefruit seed oil, hempseed oil, rose hip oil, hazelnut oil, elderberry seed oil, blackcurrant seed oil, jojoba oil, cocoa butter, coconut oil, pumpkin seed oil, linseed oil, macadamia nut oil, corn oil, mallow oil, almond oil, mango stone oil, marula oil, poppy seed oil, evening primrose oil, olive oil, palm oil, palm seed oil, peach stone oil, rambutan oil, rapeseed oil, rice bran oil, castor oil, Sacha Inchi oil, safflower oil, seabuckthorn berry oil, seabuckthorn kernel oil, sasanqua oil, sesame oil, Shea butter, soybean oil, sunflower oil, teatree oil, grape seed oil, tsubaki oil, walnut oil, wheatgerm oil, lady's smock oil and/or wild rose oil.

Preferred are amaranth seed oil, apricot kernel oil, argan oil, avocado oil, coconut oil, almond oil, macadamia nut oil, rose hip oil, sunflower oil, olive oil, peach kernel oil, jojoba oil and/or the vegetable butters Shea butter and/or cocoa butter.

The teaching as contemplated herein also comprises the fact that at least two natural vegetable oils can be mixed with one another. Preferred mixtures of natural oils can be, for example: amaranth seed oil with seabuckthorn oil, amaranth seed oil with Shea butter, amaranth seen oil with camelina oil, amaranth seed oil with olive oil, amaranth seed oil with macadamia nut oil, olive oil with seabuckthorn oil, olive oil with camelina oil, olive oil with Shea butter, macadamia nut oil with seabuckthorn oil and/or macadamia nut oil with Shea butter.

In a preferred embodiment the hair treatment agents as contemplated herein contain a mixture of natural, vegetable oils, preferably a mixture of vegetable oils and/or vegetable butters, and in particular a mixture of macadamia nut oil with Shea butter.

The one or more vegetable oil(s) (and/or butter(s)) is (are) used in the hair treatment agents as contemplated herein (in relation to the weight of the total agent) preferably in an amount from about 0.01 to about 3.00% by weight, more preferably from about 0.05 to about 2.50% by weight, particularly preferably from about 0.10 to about 2.00% by weight, very particularly preferably from about 0.25 to about 1.25 50% by weight, and in particular from about 0.50 to about 1.00% by weight.

A further preferred group of cosmetic oils are ester oils.

Particularly preferred as contemplated herein are isopropyl myristate (Rilanit® IPM), isononanoic acid-C16-18-alkyl ester (Cetiol® SN), 2-ethylhexyl palmitate (Cegesoft® 24), stearic acid-2-ethylhexyl ester (Cetiol® 868), cetyloleate, glycerine tricaprylate, coconut fatty alcohol caprinate/caprylate (Cetiol® LC), n-butylstearate, oleylerucate (Cetiol® J 600), isopropyl palmitate (Rilanit® IPP), oleyl oleate (Cetiol®), lauric acid hexyl ester (Cetiol® A), di-n-butyl adipate (Cetiol® B), myristyl myristate (Cetiol® MM), cetearyl isononanoate (Cetiol® SN), oleic acid decyl ester (Cetiol® V). Isopropyl myristate is very particularly preferred.

The one or more ester oil(s) b) is (are) used in the hair treatment agents as contemplated herein (in relation to the weight of the total agent) preferably in an amount from about 0.01 to about 4.00% by weight, more preferably from about 0.05 to about 3.50% by weight, particularly preferably from about 0.10 to about 3.00% by weight, very particularly preferably from about 0.25 to about 2.50% by weight, and in particular from about 0.50 to about 2.00% by weight.

In a further preferred embodiment the compositions as contemplated herein contain at least one natural, vegetable oil and at least one ester oil.

The compositions as contemplated herein can contain optionally one or more emulsifier(s) in order to solubilize the aforementioned oils.

Suitable emulsifiers are preferably understood to be nonionic polyethoxylated emulsifiers, particularly preferably ethoxylated fatty alcohols with from about 10 to about 24 carbon atoms and/or ethoxylated castor oil.

Suitable ethoxylated fatty alcohols as contemplated herein are addition products of ethylene oxide with a fatty alcohol, wherein the degree of ethoxylation indicates the molar amount of ethylene oxide (EO) added on average per mol of fatty alcohol. Preferred ethoxylated fatty alcohols are ethylene oxide addition products with capric alcohol, lauryl alcohol, isotridecyl alcohol, myristyl alcohol, cetyl alcohol, palmoleyl alcohol, stearyl alcohol, oleyl alcohol, elaidyl alcohol, petroselinyl alcohol, linolyl alcohol, linolenyl alcohol, elaeostearyl alcohol, arachyl alcohol, gadoleyl alcohol, behenyl alcohol, erucyl alcohol and brassidyl alcohol and technical mixtures thereof, which accumulate for example during the high-pressure hydrogenation of technical methyl esters based on fats and oils or aldehydes from oxosynthesis and also as monomer fraction during the dimerization of unsaturated fatty alcohols. Particularly preferred are addition products with technical fatty alcohols or mixtures thereof with from about 12 to about 18 carbon atoms, such as coconut, palm, palm kernel or tallow fatty alcohol, in particular coconut and/or tallow fatty alcohol.

Depending on the production method, the ethoxylated fatty alcohols accumulate as mixtures with a different distribution of the degree of ethoxylation. As contemplated herein these emulsifiers are therefore exemplified by the average degree of ethoxylation. This is usually discernible in the INCI name in the form of a number after the fatty alcohol suffix "eth". Particularly suitable ethoxylated fatty alcohols are fatty alcohols with a degree of ethoxylation from about 10 to about 100, preferably from about 20 to about 80 mol ethylene oxide per mol of fatty alcohol. Examples are Ceteaeth-12, Ceteth-15, Ceteareth-15, Laneth-16, Ceteth-16, Oleth-16, Steareth-16, Oleth-20, Ceteth-20, Ceteareth-20, Ceteareth-23, Laureth-23, Ceteareth-25, Ceteareth-30, Ceteth-40, Laneth-40, Oeth-50, Ceteareth-50, Ceteareth-60 and/or Ceteareth-80.

Suitable ethoxylated castor oil is preferably understood to mean ethoxylated, hardened (i.e. hydrogenated) and unhardened castor oil. The degree of exthoxylation specifies the molar amount of ethylene oxide (EO) added on average per mol of castor oil. Preferred ethoxylated castor oils are the compounds known under the following INCI names: PEG-5 Castor Oil, PEG-7 Hydrogenated Castor Oil, PEG-10 Hydrogenated Castor Oil, PEG-25 Hydrogenated Castor Oil, PEG-35 Castor Oil, PEG-36 Castor Oil, PEG-40 Castor Oil, PEG-40 Hydrogenated Castor Oil, PEG-50 Hydrogenated Castor Oil, PEG-60 Castor Oil, PEG-60 Hydrogenated Castor Oil, PEG-80 Castor Oil, PEG-80 Hydrogenated Castor Oil, PEG-100 Castor Oil, PEG-100 Hydrogenated Castor Oil, PEG-120 Castor Oil, PEG-120 Hydrogenated Castor Oil, PEG-150 Castor Oil, PEG-150 Hydrogenated Castor Oil, PEG-200 Castor Oil, PEG-200 Hydrogenated Castor Oil.

Preferred nonionic emulsifiers are castor oils having an average degree of ethoxylation of from about 20 to about 150, preferably from about 30 to about 100, and particularly preferably from about 35 to about 80. Particularly preferred is PEG-40 Hydrogenated Castor Oil.

It is advantageous from an ecological viewpoint of the hair treatment agents as contemplated herein contain the emulsifier(s) in small amounts, if indeed at all.

In a preferred embodiment the hair treatment agents as contemplated herein therefore preferably contain at most about 1.00% by weight, more preferably at most about 0.80% by weight, particularly preferably at most about 0.60% by weight, and in particular at most about 0.50% by weight, or one or more nonionic, ethoxylated emulsifiers (in relation to the total weight of the agent).

In order to further optimize the rheological properties of the hair treatment agents as contemplated herein, these can contain fatty substances as further active substances.

Suitable fatty substances are to be understood to be fatty acids and/or fatty alcohols which can be present both in solid form and in liquid form as an aqueous dispersion.

Linear and/or branched, saturated and/or unsaturated fatty acids having from about 6 to about 30 carbon atoms can be used as suitable fatty acids. Fatty acids having from about 10 to about 22 carbon atoms are preferred. Examples of these include isostearic acid, such as the trade products Emersol® 871 and Emersol® 875, and isopalmitic acid, such as the trade product Edenor® IP 95, and all further fatty acids sold under the trade name Edenor® (Cognis). Further typical examples of fatty acids of this kind are caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselinic acid, linoleic acid, linolenic acid, elaeostearic acid, arachinic acid, gadoleic acid, behenic acid and erucic acid and technical mixtures thereof.

The fatty acid cuts obtainable from coconut oil or palm oil are usually particularly preferred; the use of stearic acid is generally preferred in particular.

The amount of fatty acids to be used in the hair treatment agents as contemplated herein is preferably from about 0.1 to about 15% by weight, in relation to the total agent. The amount of fatty acids to be used in the hair treatment agents as contemplated herein is particularly preferably from about 0.5 to about 10% by weight, wherein amounts of from about 1 to about 5% by weight can be very particularly advantageous.

Saturated mono- or polyunsaturated, branched or unbranched fatty alcohols having from about 6 to about 30, preferably from about 10 to about 22, and very particularly preferably from about 12 to about 20 carbon atoms can be used as suitable fatty alcohols. Usable as contemplated herein are, for example, decanol, octanol, octenol, dodecenol, decenol, octadienol, dodecadienol, decadienol, oleyl alcohol, eruca alcohol, ricinol alcohol, stearyl alcohol, isostearyl alcohol, cetyl alcohol, lauryl alcohol, myristyl alcohol, arachidyl alcohol, capryl alcohol, capric alcohol, linoleyl alcohol, linolenyl alcohol and behenyl alcohol and the Guerbet alcohols thereof, wherein this list is intended to be of an exemplary rather than limiting nature.

In a preferred embodiment the fatty alcohols are obtainable from natural fatty acids, wherein it can usually be assumed that they are obtained from the esters of fatty acids by reduction. Fatty alcohol cuts that represent a mixture of different fatty alcohols likewise can be used as contemplated herein. Such substances are available to purchase for example under the names Stenol®, for example Stenol® 1618 or Lanette®, for example Lanette® O or Lorol®, for example Lorol® C8, Lorol® C14, Lorol® C18, Lorol® C8-18, HD-Ocenol®, Crodacol®, for example Crodacol® CS, Novol®, Eutanol® G, Guerbitol® 16, Guerbitol® 18, Guerbitol® 20, Isofol® 12, Isofol® 16, Isofol® 24, Isofol® 36, Isocarb® 12, Isocarb® 16 or Isocarb® 24 Of course, wool wax alcohols, as can be purchased for example under the names Corona®, White Swan®, Coronet® or Fluilan® can also be used as contemplated herein.

The amount of fatty alcohols to be used in the hair treatment agents as contemplated herein is preferably from about 0.1 to about 20% by weight, in relation to the total agent. The amount of fatty alcohols to be used in the hair treatment agents as contemplated herein is particularly preferably from about 0.5 to about 15% by weight, wherein amounts of from about 1.0 to about 10% by weight can be very particularly advantageous.

In a particularly preferred embodiment the hair treatment agents as contemplated herein contain at least on saturated or unsaturated, branched or unbranched fatty alcohol having from about 10 to about 24 carbon atoms in an amount of from about 1.00 to about 10.00% by weight (in relation to the weight of the total agent) in order to optimize the rheological properties.

Within this embodiment it is particularly preferred if the hair treatment agents as contemplated herein contain cetyl alcohol, stearyl alcohol and/or mixtures of cetyl alcohol and stearyl alcohol in the aforementioned amounts.

In a further preferred embodiment the hair treatment agents as contemplated herein can contain, in addition, at least one hydroxycarboxylic acid in a preferred amount (in relation to the weight of the total agent) of from about 0.10 to about 5.00% by weight, more preferably from about 0.20 to about 4.00% by weight, particularly preferably from about 0.30 to about 3.00% by weight, and in particular from about 0.40 to about 2.00% by weight in order to adjust the pH value, but at the same time also in order to support the haircare properties.

Suitable hydroxycarboxylic acids are preferably understood to be alpha-hydroxycarboxylic acids and in particular—for example in fruit acids—naturally occurring alpha-hydroxycarboxylic acids.

These include, for example, malic acid, citric acid, glycolic acid, isocitric acid, mandelic acid, lactic acid, tartronic acid and/or tartaric acid.

Suitable hydroxycarboxylic acids are also understood to be the dicarboxylic acids glutaminic acid and/or succinic acid.

Citric acid, lactic acid, glutaminic acid and/or succinic acid are particularly preferred.

Particularly good stability and particularly good haircare results (in particular in respect of the hair shine and the sensory properties, such as softness and smoothness) without overconditioning (oily, weighted-down hair) can be attained if the hair treatment agents as contemplated herein, besides the aforementioned active substances, do not contain any further fatty phase constituents—in particular no silicone oils and/or mineral oils.

In a further preferred embodiment, hair treatment agents as contemplated herein are therefore substantially free from silicones and/or mineral oils.

The term "substantially free" is understood to mean that the hair treatment agents as contemplated herein preferably contain less than about 0.25% by weight of, more preferably less than about 0.10% by weight of, and in particular no silicones and/or mineral oils (in relation to the total weight of the hair cleansing agents).

The aforementioned amounts apply here both for freely added silicone and/or mineral oil and for silicones and/or mineral oils which might be contained in trade products as by-product.

In a further preferred embodiment, hair treatment agents as contemplated herein are substantially free from polymeric thickeners of synthetic and/or natural origin.

The term "substantially free" is understood to mean that the hair treatment agents as contemplated herein preferably contain less than about 0.25% by weight of, more preferably less than about 0.10% by weight of, and in particular no polymeric thickeners of synthetic and/or natural origin (in relation to the total weight of the hair cleansing agents).

The aforementioned amounts apply here both for freely added polymeric thickeners of synthetic and/or natural origin and for polymeric thickeners of synthetic and/or natural origin which might be contained in trade products as by-product.

The hair treatment agents as contemplated herein may contain further optional active substance, provided these do not hinder the efficacy or the production of the agents. The optional active substances include, for example,
protein hydrolyzates,
vitamins,
anti-dandruff active substances,
carbohydrates,
bioquinones,
purines,
ectoine and/or
plant extracts.

Suitable protein hydrolyzates are to be understood to be product mixtures that can be obtained by acid-, base- or enzyme-catalyzed degradation of proteins.

Protein hydrolyzates of plant, animal and/or marine origin can be used.

Animal protein hydrolyzates are, for example, elastin, collagen, keratin, silk and milk protein hydrolyzates, which can also be present in the form of salts. Such products are sold for example under the trade names Dehylan® (Cognis), Promois® (Interorgana), Collapuron® (Cognis), Nutrilan® (Cognis), Gelita-Sol® (Deutsche Gelatine Fabriken Stoess & Co), Lexein® (Inolex) and Kerasol® (Croda).

Protein hydrolyzates of plant origin are preferred, for example soy, almond, rice, pea, potato and wheat protein hydrolyzates. Such products are obtainable for example under the trade names Gluadin® (Cognis), DiaMin® (Diamalt), Lexein® (Inolex) and Crotein® (Croda).

Cationized protein hydrolyzates can also be used, wherein the basic protein hydrolyzate can originate from animals, for example from collagen, milk or keratin, from plants, for example from wheat, maize, rice, potatoes, soya or almonds, from marine life, for example from fish collagen or algae, or from biotechnologically obtained protein hydrolyzates. The protein hydrolyzates forming the basis of the cationic derivatives can be obtained from the corresponding proteins by a chemical hydrolysis, particularly alkaline or acid hydrolysis, by an enzymatic hydrolysis and/or a combination of both types of hydrolysis. The hydrolysis of proteins generally produces a protein hydrolyzate with a molecular weight distribution from about 100 daltons up to several thousand daltons. Cationic protein hydrolyzates that are preferred are those of which the base protein content has a molecular weight of from about 100 to about 25,000 daltons, preferably from about 250 to about 5,000 daltons. Moreover, cationic protein hydrolyzates are understood to include quaternized amino acids and their mixtures. Quaternization of the protein hydrolyzates or the amino acids is often carried out using quaternary ammonium salts such as N,N-dimethyl-N-(n-alkyl)-N-(2-hydroxy-3-chloro-n-propyl) ammonium halides. Moreover, the cationic protein hydrolyzates can also be further derivatized. Typical examples of cationic protein hydrolyzates and derivatives are the commercially available products known under the following INCI names: Cocodimonium Hydroxypropyl Hydrolyzed Collagen, Cocodimopnium Hydroxypropyl Hydrolyzed Casein, Cocodimonium Hydroxypropyl Hydrolyzed Collagen, Cocodimonium Hydroxypropyl Hydrolyzed Hair Keratin, Cocodimonium Hydroxypropyl Hydrolyzed Keratin, Cocodimonium Hydroxypropyl Hydrolyzed Rice Protein, Cocodimonium Hydroxypropyl Hydrolyzed Silk, Cocodimonium Hydroxypropyl Hydrolyzed Soy Protein, Cocodimonium Hydroxypropyl Hydrolyzed Wheat Protein, Cocodimonium Hydroxypropyl Silk Amino Acids, Hydroxypropyl Arginine Lauryl/Myristyl Ether HCl, Hydroxypropyltrimonium Gelatin, Hydroxypropyltrimonium Hydrolyzed Casein, Hydroxypropyltrimonium Hydrolyzed Collagen, Hydroxypropyltrimonium Hydrolyzed Conchiolin Protein, Hydroxypropyltrimonium Hydrolyzed keratin, Hydroxypropyltrimonium Hydrolyzed Rice Bran Protein, Hydroxyproypltrimonium Hydrolyzed Silk, Hydroxypropyltrimonium Hydrolyzed Soy Protein, Hydroxypropyl Hydrolyzed Vegetable Protein, Hydroxypropyltrimonium Hydrolyzed Wheat Protein, Hydroxypropyltrimonium Hydrolyzed Wheat Protein/Siloxysilicate, Laurdimonium Hydroxypropyl Hydrolyzed Soy Protein, Laurdimonium Hydroxypropyl Hydrolyzed Wheat Protein, Laurdimonium Hydroxypropyl Hydrolyzed Wheat Protein/Siloxysilicate, Lauryldimonium Hydroxypropyl Hydrolyzed Casein, Lauryldimonium Hydroxypropyl Hydrolyzed Collagen, Lauryldimonium Hydroxypropyl Hydrolyzed Keratin, Lauryldimonium Hydroxypropyl Hydrolyzed Silk, Lauryldimonium Hydroxypropyl Hydrolyzed Soy Protein, Steardimonium Hydroxypropyl Hydrolyzed Casein, Steardimonium Hydroxypropyl Hydrolyzed Collagen, Steardimonium Hydroxypropyl Hydrolyzed Keratin, Steardimonium Hydroxypropyl Hydrolyzed Rice Protein, Steardimonium Hydroxypropyl Hydrolyzed Silk, Steardimonium Hydroxypropyl Hydrolyzed Soy Protein, Steardimonium Hydroxypropyl Hydrolyzed Vegetable Protein, Steardimonium Hydroxypropyl Hydrolyzed Wheat Protein, Steartrimonium Hydroxyethyl Hydrolyzed Collagen, Quaternium-76 Hydrolyzed Collagen, Quaternium-79 Hydrolyzed Collagen, Quaternium-79 Hydrolyzed Keratin, Quaternium-79 Hydrolyzed Milk Protein, Quaternium-79 Hydrolyzed Silk, Quaternium-79 Hydrolyzed Soy Protein, Quaternium-79 Hydrolyzed Wheat Protein.

The weight share of the protein hydrolyzate(s) in the total weight of the hair treatment agents can be preferably from about 0.01 to about 5% by weight, more preferably from about 0.025 to about 3% by weight, and in particular from about 0.05 to about 2% by weight.

Suitable vitamins are preferably understood to mean the following vitamins, provitamins and vitamin precursors and derivatives thereof:

Vitamin A: the group of substances referred to as vitamin A includes retinol (Vitamin $A_1$) and 3,4-didehydroretinol (Vitamin $A_2$). β-carotin is the provitamin of retinol. Examples of suitable vitamin A components include vitamin A acid and esters thereof, vitamin A aldehyde, and vitamin A alcohol as well as esters thereof, such as the palmitate and acetate.

Vitamin B: the vitamin B group or the vitamin B complex includes, inter alia,
vitamin $B_1$ (thiamin)
vitamin $B_2$ (riboflavin)
vitamin $B_3$. This often includes the compounds of nicotinic acid and nicotinic acid amide (niacinamide).
vitamin $B_5$ (pantothenic acid and panthenol). In the context of this group, panthenol is preferably used. Useable derivatives of panthenol are especially the esters and ethers of panthenol, pantolactone, and also cationically derivatized panthenols. Specific representatives are, for example, panthenol triacetate, panthenol monoethyl ether and monoacetate thereof, as well as cationic panthenol derivatives.
vitamin $B_6$ (pyridoxine and also pyridoxamine and pyridoxal).

Vitamin C (ascorbic acid): the use in the form of the palmitic acid ester, the glucosides, or phosphates can be preferred. The use in combination with tocopherols can also be preferred.

Vitamin E

Vitamin F: the term "vitamin F" is usually understood to mean essential fatty acids, in particular linoleic acid, linolenic acid and arachidonic acid.

Vitamin H: The compound (3aS,4S, 6aR)-2-oxohexahydrothienol[3,4-d]-imidazol-4-valeric acid denotes vitamin H, for which the trivial name however (biotin) has become accepted.

Vitamins, provitamins and vitamin precursors from the groups A, B, E and H are particularly preferred. Nicotinic acid amide, biotin, pantolactone and/or panthenol are preferred in particular.

The weight share of the vitamin(s), vitamin derivative(s), and/or the vitamin precursor(s) in the total weight of the hair treatment agent is preferably from about 0.001 to about 2% by weight, particularly preferably from about 0.005 to about 1% by weight, and in particular from about 0.01 to about 0.5% by weight.

Suitable anti-dandruff active substances can be selected from piroctone olamines, climbazole, zinc pyrithione, ketoconazoles, salicylic acid, sulfur, selenium sulfide, tea preparations, undecenoic acid derivatives, burdock extracts, poplar extracts, stinging nettle extracts, walnut shell extracts, birch extracts, willow bark extracts, rosemary extracts and/or arnica extracts. Climbazole, zinc pyrithione, and piroctone olamines are preferred. Zinc pyrithione is preferred in particular.

The weight share of anti-dandruff agents in the total weight of the hair treatment agent can be preferably from about 0.01 to about 10% by weight, more preferably from about 0.025 to about 7.5% by weight, particularly preferably from about 0.05 to about 5% by weight, and in particular from about 0.075 to about 3% by weight.

Suitable carbohydrates can be selected from the group of monosaccharides and/or disaccharides and preferably can be used in the hair treatment agents as contemplated herein in an amount of from about 0.01 to about 5.00% by weight, particularly preferably from about 0.05 to about 4.50% by weight, and in particular from about 0.10 to about 2.50% by weight (in relation to the total weight of the agent).

Preferred monosaccharides and/or disaccharides are:
monosaccharides such as d-ribose and/or d-xylose and/or I-arabinose and/or D-glucose and/or d-mannose and/or d-galactose and/or d-fructose and/or sorbose and/or I-fucose and/or I-rhamnose and disaccharides such as sucrose and/or maltose and/or lactose and/or trehalose and/or cellobiose and/or gentobiose and/or isomaltose.

In the agents as contemplated herein, suitable bioquinones are understood to be one or more ubiquinone(s) and/or plastoquinone(s). The ubiquinones preferred as contemplated herein have the following formula:

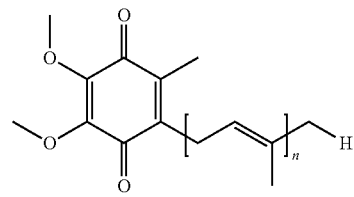

with n=6, 7, 8, 9 or 10.

The coenzyme Q-10 is more preferred here.

Bioquinones, in particular coenzyme Q-10, can be used in the hair treatment agents as contemplated herein (in relation to the total weight thereof) preferably in an amount from about 0.001 to about 1.0% by weight.

Suitable purine and/or purine derivatives can be used in the hair treatment agents as contemplated herein (in relation to the total weight thereof) preferably in an amount from about 0.001 to about 2.5% by weight. Cosmetic agents that are preferred as contemplated herein are exemplified in that they contain purine, adenine, guanine, uric acid, hypoxanthine, 6-purinthiol, 6-thioguanine, xanthine, caffeine, theobromine or theophylline. Caffeine is most preferred.

Ectoine ((S)-2-methyl-1,4,5,6-tetrahydro-4-pyrimidine carboxylic acid can be used in the hair treatment agents as contemplated herein (in relation to the total weight thereof) preferably in an amount from about 0.00001 to about 1.0% by weight.

By use of plant extracts as nourishing substances, the hair treatment agents as contemplated herein can be formulated in a particularly near-natural manner and yet very effectively in respect of their nourishing performance. As appropriate, it is even possible to dispense with preservatives which are otherwise conventional. As contemplated herein, the extracts from green tea, oak bark, stinging nettle, witch hazel, hops, henna, chamomile, burdock, horsetail, hawthorn, linden blossom, almond, aloe vera, pine needles, horse chestnut, sandalwood, juniper, coconut, mango, apricot, lemon, wheat, kiwi, melon, orange, grapefruit, sage, rosemary, birch, mallow, valerian, lady's smock, wild thyme, yarrow, thyme, lemon balm, restharrow, coltsfoot, marshmallow, meristem, ginseng, coffee, cocoa, moringa, ginger root and ayurvedic plant extracts such as aegle marmelos (bilwa), *Cyperus rotundus* (nagar motha), emblica officinalis (amalki) morida citrifolia (ashyuka), tinospora cordifolia (guduchi), santalum album, (chan dana), crocus sativus (kumkuma), cinnamonum zeylanicum and *Nelumbo nucifera* (kamala), grasses such as wheat, barley, rye, oats, spelt, corn, the different varieties of millet (proso millet, finger millet, foxtail millet as examples), sugar cane, rye grass, meadow foxtail, oat grass, bent grass, meadow fescue, moor grass, bamboo, cotton grass, Pennisetum, Andropogonodeae (called Imperata cylindrica and flames grass or cogon grass), buffalo grass, Spartina, cynodon, love grasses, cymbopogon (lemon grass), oryzeae (rice), Zizania (wild rice), beach grass, shrubs oats, holcus, dither grasses, bluegrasses, couch grass and Echinacea, in particular Echinacea purpurea (L.), all kinds of wine and pericarp of Litchie chinensis are preferred in particular.

The plant extracts can be used both in pure and diluted form. If used in diluted form, they usually contain approximately 2 to about 80% by weight of active substance and, as solvent, the extracting agent or extracting agent mixture used for their recovery.

The cosmetic agents can also contain further active substances, auxiliaries and additives, such as UV filter substances,
structurants, such as maleic acid and lactic acid,
swelling agents, such as urea, allantoin, carbonates or hydantoin,
dyes for coloring the agent, wherein this is not preferred as contemplated herein,
complexing agents, such as EDTA, NTA, β-alanine diacetic acid and phosphonic acids,
pearlescent agents, such as ethylene glycol mono- and distearate,
pigments,
propellants, such as propane-butane mixtures, $N_2O$, dimethylether, $CO_2$ and air,
antioxidants,
perfume oils, fragrances and aromatic substances, wherein this is not preferred as contemplated herein if the perfume oils, fragrances and aromatic substances are synthetic.

The hair treatment agents as contemplated herein preferably have a pH value ranging from about 2.5 to about 5.0, more preferably from about 3.0 to about 4.5 and in particular from about 3.5 to about 4.5.

Hair treatment agents preferred as contemplated herein have a viscosity ranging from about 3,000 to about 20,000 mPas, more preferably from about 3,500 to about 15,000 mPas and in particular from about 4,000 to about 12,000 mPas (measured using Brookfield DV 2+; 2 rpm; spindle 5; about 20° C.).

The hair treatment agents as contemplated herein can be present both in single-phase or multi-phase form, for example in particular with two or three optically clearly separated discrete phases. If the compositions are present in multi-phase form the entire composition is transferred into a single-phase composition by shaking prior to use and is applied in this form. After shaking the mixture spontaneously separates again, and the discrete phases re-form within approximately 1 minute to about 300 minutes. If the composition is present in multi-phase form it is packaged in optically transparent packaging.

The compositions as contemplated herein may also be provided in the form of a pump spray, aerosol spray, pump mousse or aerosol mousse.

A second subject of the present disclosure is the cosmetic use of the hair treatment agent as contemplated herein to improve the nourishment properties of hair, in particular to improve the combability and ease of detangling of wet and dry hair, and also the feel, shine and static properties of hair.

That which has been said with regard to the agents as contemplated herein applies, mutatis mutandis, with regard to preferred embodiments of the use as contemplated herein.

The following examples are intended to explain the subject matter of the present disclosure without limiting it.

EXAMPLES

TABLE

Composition 46 is as contemplated herein; compositions 47 and 48 are comparison compositions a) The following hair rinses were prepared as contemplated herein (the stated values are in % by weight):

| | 1 | 2 | 3 | 4 | 5 |
|---|---|---|---|---|---|
| Trimethylglycine | 0.05-10.00 | 0.10-8.00 | 0.50-6.00 | 0.75-5.00 | 1.00-4.00 |
| Amidoamine b) of formula (I) | 0.01-2.00 | 0.05-1.75 | 0.10-1.50 | 0.20-1.25 | 0.25-1.00 |
| Esterquat c) of formula (II) | 0.01-10.00 | 0.05-8.00 | 0.10-6.00 | 0.20-4.00 | 0.25-2.00 |
| Water and any further auxiliaries and additives | to 100 | to 100 | to 100 | to 100 | to 100 |

TABLE-continued

Composition 46 is as contemplated herein; compositions 47 and 48 are comparison compositions

| | 6 | 7 | 8 | 9 | 10 |
|---|---|---|---|---|---|
| Trimethylglycine | 0.05-10.00 | 0.10-8.00 | 0.50-6.00 | 0.75-5.00 | 1.00-4.00 |
| Amidoamine b) of formula (I) | 0.01-2.00 | 0.05-1.75 | 0.10-1.50 | 0.20-1.25 | 0.25-1.00 |
| Esterquat c) of formula (II) | 0.01-10.00 | 0.05-8.00 | 0.10-6.00 | 0.20-4.00 | 0.25-2.00 |
| Vegetable oil and/or vegetable butter | 0.01-3.00 | 0.05-2.50 | 0.10-2.00 | 0.25-1.50 | 0.50-1.00 |
| Water and any further auxiliaries and additives | to 100 | to 100 | to 100 | to 100 | to 100 |

| | 11 | 12 | 13 | 14 | 15 |
|---|---|---|---|---|---|
| Trimethylglycine | 0.05-10.00 | 0.10-8.00 | 0.50-6.00 | 0.75-5.00 | 1.00-4.00 |
| Amidoamine b) of formula (I) | 0.01-2.00 | 0.05-1.75 | 0.10-1.50 | 0.20-1.25 | 0.25-1.00 |
| Esterquat c) of formula (II) | 0.01-10.00 | 0.05-8.00 | 0.10-6.00 | 0.20-4.00 | 0.25-2.00 |
| Polyol | 0.50-10.00 | 0.75-9.00 | 1.00-6.00 | 1.50-5.00 | 2.00-4.00 |
| Water and any further auxiliaries and additives | to 100 | to 100 | to 100 | to 100 | to 100 |

| | 16 | 17 | 18 | 19 | 20 |
|---|---|---|---|---|---|
| Trimethylglycine | 0.05-10.00 | 0.10-8.00 | 0.50-6.00 | 0.75-5.00 | 1.00-4.00 |
| Amidoamine b) of formula (I) | 0.01-2.00 | 0.05-1.75 | 0.10-1.50 | 0.20-1.25 | 0.25-1.00 |
| Esterquat c) of formula (II) | 0.01-10.00 | 0.05-8.00 | 0.10-6.00 | 0.20-4.00 | 0.25-2.00 |
| $C_{10}$-$C_{24}$ fatty alcohol | 0.10-20.00 | 0.50-15.00 | 1.00-12.50 | 1.50-10.00 | 2.00-8.00 |
| Water and any further auxiliaries and additives | to 100 | to 100 | to 100 | to 100 | to 100 |

| | 21 | 22 | 23 | 24 | 25 |
|---|---|---|---|---|---|
| Trimethylglycine | 0.05-10.00 | 0.10-8.00 | 0.50-6.00 | 0.75-5.00 | 1.00-4.00 |
| Amidoamine b) of formula (I) | 0.01-2.00 | 0.05-1.75 | 0.10-1.50 | 0.20-1.25 | 0.25-1.00 |
| Esterquat c) of formula (II) | 0.01-10.00 | 0.05-8.00 | 0.10-6.00 | 0.20-4.00 | 0.25-2.00 |
| Hydroxycarboxylic acid | 0.10-5.00 | 0.20-4.00 | 0.30-3.00 | 0.40-2.00 | 0.50-1.00 |
| Water and any further auxiliaries and additives | to 100 | to 100 | to 100 | to 100 | to 100 |

| | 26 | 27 | 28 | 29 | 30 |
|---|---|---|---|---|---|
| Trimethylglycine | 0.05-10.00 | 0.10-8.00 | 0.50-6.00 | 0.75-5.00 | 1.00-4.00 |
| Amidoamine b) of formula (I) | 0.01-2.00 | 0.05-1.75 | 0.10-1.50 | 0.20-1.25 | 0.25-1.00 |
| Esterquat c) of formula (II) | 0.01-10.00 | 0.05-8.00 | 0.10-6.00 | 0.20-4.00 | 0.25-2.00 |
| Vegetable oil and/or vegetable butter | 0.01-3.00 | 0.05-2.50 | 0.10-2.00 | 0.25-1.50 | 0.50-1.00 |
| Polyol | 0.50-10.00 | 0.75-9.00 | 1.00-6.00 | 1.50-5.00 | 2.00-4.00 |
| Water and any further auxiliaries and additives | to 100 | to 100 | to 100 | to 100 | to 100 |

| | 31 | 32 | 33 | 34 | 35 |
|---|---|---|---|---|---|
| Trimethylglycine | 0.05-10.00 | 0.10-8.00 | 0.50-6.00 | 0.75-5.00 | 1.00-4.00 |
| Amidoamine b) of formula (I) | 0.01-2.00 | 0.05-1.75 | 0.10-1.50 | 0.20-1.25 | 0.25-1.00 |
| Esterquat c) of formula (II) | 0.01-10.00 | 0.05-8.00 | 0.10-6.00 | 0.20-4.00 | 0.25-2.00 |
| Vegetable oil and/or vegetable butter | 0.01-3.00 | 0.05-2.50 | 0.10-2.00 | 0.25-1.50 | 0.50-1.00 |

TABLE-continued

Composition 46 is as contemplated herein; compositions 47 and 48 are comparison compositions

| | | | | | |
|---|---|---|---|---|---|
| $C_{10}$-$C_{24}$ fatty alcohol | 0.10-20.00 | 0.50-15.00 | 1.00-12.50 | 1.50-10.00 | 2.00-8.00 |
| Water and any further auxiliaries and additives | to 100 | to 100 | to 100 | to 100 | to 100 |

| | 36 | 37 | 38 | 39 | 40 |
|---|---|---|---|---|---|
| Trimethylglycine | 0.05-10.00 | 0.10-8.00 | 0.50-6.00 | 0.75-5.00 | 1.00-4.00 |
| Amidoamine b) of formula (I) | 0.01-2.00 | 0.05-1.75 | 0.10-1.50 | 0.20-1.25 | 0.25-1.00 |
| Esterquat c) of formula (II) | 0.01-10.00 | 0.05-8.00 | 0.10-6.00 | 0.20-4.00 | 0.25-2.00 |
| Vegetable oil and/or vegetable butter | 0.01-3.00 | 0.05-2.50 | 0.10-2.00 | 0.25-1.50 | 0.50-1.00 |
| Hydroxycarboxylic acid | 0.10-5.00 | 0.20-4.00 | 0.30-3.00 | 0.40-2.00 | 0.50-1.00 |
| Water and any further auxiliaries and additives | to 100 | to 100 | to 100 | to 100 | to 100 |

| | 41 | 42 | 43 | 44 | 45 |
|---|---|---|---|---|---|
| Trimethylglycine | 0.05-10.00 | 0.10-8.00 | 0.50-6.00 | 0.75-5.00 | 1.00-4.00 |
| Amidoamine b) of formula (I) | 0.01-2.00 | 0.05-1.75 | 0.10-1.50 | 0.20-1.25 | 0.25-1.00 |
| Esterquat c) of formula (II) | 0.01-10.00 | 0.05-8.00 | 0.10-6.00 | 0.20-4.00 | 0.25-2.00 |
| Vegetable oil and/or vegetable butter | 0.01-3.00 | 0.05-2.50 | 0.10-2.00 | 0.25-1.50 | 0.50-1.00 |
| Polyol | 0.50-10.00 | 0.75-9.00 | 1.00-6.00 | 1.50-5.00 | 2.00-4.00 |
| $C_{10}$-$C_{24}$ fatty alcohol | 0.10-20.00 | 0.50-15.00 | 1.00-12.50 | 1.50-10.00 | 2.00-8.00 |
| Hydroxycarboxylic acid | 0.10-5.00 | 0.20-4.00 | 0.30-3.00 | 0.40-2.00 | 0.50-1.00 |
| Water and any further auxiliaries and additives | to 100 | to 100 | to 100 | to 100 | to 100 | b) Assessment of hair cleansing agents as contemplated herein and not as contemplated herein

| | 46 | 47 | 48 |
|---|---|---|---|
| Cetearyl Alcohol | 5.00 | 3.50 | 5.00 |
| Glycerol | 3.00 | | |
| Betaine (Trimethylgycine) | 1.50 | | |
| Isopropyl Myristate | 1.00 | 1.00 | |
| Caprylic/Capric Triglyceride | | | 1.00 |
| Glyceryl Stearate | | 0.60 | |
| Distearoylethyl Hydroxyethylmonium Methosulfate, Cetearyl Alcohol | | | 1.50 |
| Behentrimonium Chloride | | 2.00 | 1.00 |
| Behenoyl PG-Trimonium Chloride | | | 2.50 |
| Bis(Isostearoyl/Oleoyl Isopropyl)Dimonium Methosulfate | 1.00 | | |
| *Butyrospermum Parkii* Butter | 0.80 | | |
| Citric Acid | | 0.50 | 0.30 |
| Lactic Acid | 0.72 | | |
| Brassicamidopropyl Dimethylamine | 0.40 | | 0.80 |
| Stearamidopropyl Dimethylamine | | 0.40 | |
| Sodium Benzoate | 0.35 | | |
| Sodium Methylparabene | | 0.25 | |
| Perfume | 0.55 | 0.55 | 0.55 |
| Ceteareth-20 | 0.20 | | |
| Polyquaternium-37, Dicaprylyl Carbonate, Lauryl Glucoside | | 0.50 | |
| Guar Hydroxypropyltrimonium Chloride | | | 0.10 |
| Phenoxyethanol | | 0.50 | 0.75 |
| Ethylhexylglycerin | | | 0.20 |

TABLE-continued

Composition 46 is as contemplated herein; compositions 47 and 48 are comparison compositions

| | | | |
|---|---|---|---|
| Macadamia nut oil | 0.20 | 0.20 | 0.20 |
| Water | to 100 | to 100 | to 100 |
| Sum of cationic nourishing substances | 1.00 | 1.85 | 2.97 |
| pH value | 3.5-4.5 | 3.5-4.5 | 3.5-4.5 |
| Viscosity [mPas]* | 4.000-12.000 | 4.000-12.000 | 4.000-12.000 |
| Satisfaction with the nourishing properties (average)** | 5.1 | 4.7 | 4.9 |
| Satisfaction with the hair shine (average)** | 4.9 | 4.7 | 4.8 |

*measured using Brookfield DV 2+; 20 rpm; spindle 5; 20° C.
**The specified value corresponds to the mean value of the corresponding absolute valuation of 20

Test subjects who scored from 1 to 7 (with 1=not at all; 7=entirely satisfied) in response to the question: "How satisfied are you with the shine properties of the product?" and "How satisfied are you with the nourishing properties of the product?" after having used the various products for two weeks each. The products were packaged neutrally prior to the test and coded accordingly.

The results in Table 1 show that the compositions as contemplated herein provide improved nourishing properties on the hair compared to compositions from the prior art, although they contain barely half or a third of the cationic nourishing substances.

The invention claimed is:

1. A hair treatment agent comprising, in relation to a total weight of the hair treatment agent,
   a) about 1.50% by weight of trimethylglycine,
   b) about 1.00% by weight of Bis(Isostearoyl/Oleyl Isopropyl) Dimonium Methosulfate,
   c) about 0.40% by weight of Brassicamidopropyl Dimethylamine
   d) about 5.00% by weight of cetearyl alcohol,
   e) about 3.00% by weight of glycerol,
   f) about 1.00% by weight of isopropyl myristate,
   g) about 0.80% by weight of butyrospermum parkii butter,
   h) lactic acid,
   i) sodium benzoate,
   j) perfume,
   k) ceteareth-20,
   l) macadamia nut oil, and
   m) water.

2. The hair treatment agent of claim 1, wherein the hair treatment agent consists of a)-m).

* * * * *